United States Patent
Locke et al.

(10) Patent No.: US 11,413,389 B2
(45) Date of Patent: Aug. 16, 2022

(54) MULTI-ORIENTATION FLUID MANAGEMENT

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 257 days.

(21) Appl. No.: 15/741,578

(22) PCT Filed: Jul. 1, 2016

(86) PCT No.: PCT/US2016/040817
§ 371 (c)(1),
(2) Date: Jan. 3, 2018

(87) PCT Pub. No.: WO2017/007724
PCT Pub. Date: Jan. 12, 2017

(65) Prior Publication Data
US 2018/0200419 A1    Jul. 19, 2018

Related U.S. Application Data

(60) Provisional application No. 62/189,609, filed on Jul. 7, 2015.

(51) Int. Cl.
*A61M 1/00* (2006.01)
*A61F 13/00* (2006.01)

(52) U.S. Cl.
CPC ......... *A61M 1/88* (2021.05); *A61F 13/00068* (2013.01); *A61M 1/0001* (2013.01);
(Continued)

(58) Field of Classification Search
CPC .............. A61M 1/0094; A61M 1/0001; A61M 2205/7536; A61M 1/0017; A61M 1/0052;
(Continued)

(56) References Cited

U.S. PATENT DOCUMENTS 1,355,846 A    10/1920  Rannells
2,547,758 A     4/1951  Keeling
(Continued)

FOREIGN PATENT DOCUMENTS

AU    550575 B2    3/1986
AU    745271 B2    3/2002
(Continued)

OTHER PUBLICATIONS

Eastman, Eastman TRITAN copolyester, Redefining the balance between toughness and heat resistance., Feb. 2010 (Year: 2010).*
(Continued)

*Primary Examiner* — Tatyana Zalukaeva
*Assistant Examiner* — Meagan Ngo

(57) ABSTRACT

Apparatuses for multi-orientation fluid management are described. In some example embodiments, an apparatus for managing fluids may comprise an absorbent core and one or more layers of a fluid acquisition and manifolding material. The fluid acquisition and manifolding material can provide a shell or envelope for capturing the fluid and distributing it to the absorbent core for storage. The manifolding material
(Continued)

can distribute fluid as the absorbent core swells. The apparatus may additionally include an exudate container providing a casing for the absorbent core and the fluid acquisition and manifolding layers.

21 Claims, 8 Drawing Sheets

(52) U.S. Cl.
CPC .............. *A61M 1/784* (2021.05); *A61M 1/90* (2021.05); *A61M 2205/21* (2013.01); *A61M 2205/7527* (2013.01); *A61M 2205/7536* (2013.01)

(58) Field of Classification Search
CPC ........ A61M 1/0088; A61M 2205/7527; A61M 2205/21; A61M 1/0023; A61M 1/0049; A61M 1/0096; A61M 1/88; A61F 13/00068; A61F 13/00004; A61F 13/00008
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2013/0053797 A1* | 2/2013 | Locke ................. A61M 1/0027 604/319 |
| 2013/0053798 A1* | 2/2013 | Coulthard ............. A61M 27/00 604/319 |
| 2014/0163491 A1 | 6/2014 | Schuessler et al. |
| 2014/0200533 A1 | 7/2014 | Whyte et al. |
| 2014/0350494 A1* | 11/2014 | Hartwell ................ A61F 13/022 604/319 |

(56) References Cited

U.S. PATENT DOCUMENTS

| | | | | |
|---|---|---|---|---|
| 2014/0350496 | A1* | 11/2014 | Riesinger | A61F 13/0209 604/319 |
| 2015/0080788 | A1 | 3/2015 | Blott et al. | |
| 2015/0202353 | A1* | 7/2015 | Daughtery | A61M 1/0088 604/319 |
| 2016/0375183 | A1* | 12/2016 | Chen | A61M 1/0094 128/848 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2010/056977 A2 | 5/2010 |
| WO | 2012/142002 A1 | 10/2012 |
| WO | 2013/032539 A1 | 3/2013 |
| WO | 2014/140606 A1 | 9/2014 |
| WO | 2014/158529 A1 | 10/2014 |

OTHER PUBLICATIONS

ISR and Written Opinion for corresponding PCT/US2016/040817 dated Oct. 6, 2016.

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Japanese Notice of Rejection for Corresponding Application No. 2017-568196, dated Jun. 9, 2020.

Japanese Notice of Rejection for Corresponding Application No. 2017-568196, dated Feb. 16, 2021.

* cited by examiner

MULTI-ORIENTATION FLUID MANAGEMENT

RELATED APPLICATIONS

This application claims the benefit, under 35 USC 119(e), of the filing of U.S. Provisional Patent Application No. 62/189,609, entitled "Multi-Orientation Fluid Management", filed Jul. 7, 2015, which is incorporated herein by reference for all purposes.

TECHNICAL FIELD

The invention set forth in the appended claims relates generally to tissue treatment systems and more particularly, but without limitation, to containers adapted for multi-orientation fluid management in a negative-pressure wound therapy system.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for managing fluids in a negative-pressure therapy environment are set forth in the appended claims. Illustrative embodiments are also provided to enable a person skilled in the art to make and use the claimed subject matter.

For example, in some embodiments, an apparatus for managing fluids may comprise an absorbent core and one or more layers of a fluid acquisition and manifolding material. The fluid acquisition and manifolding material can be formed into a shell around the absorbent core in some embodiments. The absorbent core may be a super-absorbent polymer, and the shell is preferably adapted to expand or inflate as the absorbent core absorbs liquid. For example, the shell may initially be much larger than the absorbent core. In some embodiments, the absorbent core may comprise absorbent particles, and the shell may be adapted to retain the superabsorbent particles, particularly as they swell. A shell having pores in a range of about 50 microns to 400 microns may be suitable for some embodiments. In some embodiments, the shell may have more than one layer, such as an inner layer and an outer layer, wherein the inner layer may have smaller pores than the outer layer. For example, an inner layer may have pores suitable for retaining absorbent particles, such as about 50 microns, and an outer layer may have a larger pore size, such as about 400 microns.

The shell and the absorbent core may be disposed in a container adapted for storing exudate or other fluid. Under negative pressure, a container can initially provide a dead-space around the shell and the absorbent core, providing room to expand and maintain capacity. For example, the shell and the absorbent core may be sized to expand or inflate such that the capacity of the container is reached. The shell is also preferably shaped for appropriate fit with the container so that the shell presses against all surfaces of the container if the absorbent core is saturated. The capacity of the absorbent core may be selected based on the type of tissue or anticipated exudate volume, for example.

If fluid enters the container, the fluid acquisition and manifolding material can capture the fluid and distribute the fluid to the absorbent core for storage. As the absorbent core swells, the manifolding material can continue to distribute fluid. Negative pressure can be transmitted from a singular filter at a canister port, initially by virtue of an open volume in the container and by virtue of the manifolding properties of the shell as the absorbent core swells and pushes the shell against the walls of the container.

The container may have a lid, cap, base, or other portion that can be detachably sealed and secured. For example, a locking mechanism may hold a lid or door on a rigid portion of the container, and a flexible sealing gasket can be held under compression to prevent leaks in operation. A saturated absorbent core and shell could be removed and replaced, allowing the container or parts thereof to be used more than once.

More generally, the apparatus may be an exudate container comprising a casing, an absorbent core disposed within the casing, and a manifold disposed in the casing around the absorbent core. The hydrophobicity may increase from a first surface to a second surface of the manifold. For example, the manifold may have a first side that is hydrophobic and a second side that is hydrophilic. In some embodiments, the manifold may comprise a distribution envelope, wherein the distribution envelope has a hydrophobic internal surface and a hydrophilic external surface. In other example embodiments, the first side may be a side of a hydrophobic layer, and the second side may be a side of a hydrophilic layer. In some embodiments, the manifold may comprise a textile of polyester fibers, which may be woven or non-woven. For example, the manifold may comprise or consist essentially of a non-woven textile in some embodiments. In more specific example embodiments, the manifold may comprise or consist essentially of a dual-layer non-woven textile, wherein a first layer is hydrophobic and a second layer is hydrophilic. The absorbent core may be a super-absorbent polymer in some embodiments. The exudate container may also comprise at least two ports adapted to provide a fluid path into and out of the container, and the manifold may be configured to provide a fluid path between the ports around the absorbent core.

Other example embodiments may include an apparatus for providing negative-pressure therapy. In some embodiments, the apparatus may comprise a negative-pressure source and a container fluidly coupled to the negative-pressure source. An absorbent core may be disposed in the container, and a hydrophobic layer may be disposed adjacent to the absorbent core. A hydrophilic layer may also be disposed in the container adjacent to the hydrophobic layer.

The absorbent core may be a super-absorbent polymer in some embodiments. The container may have an outlet port and an inlet port. The hydrophilic layer, the hydrophobic layer, or both may be adapted to manifold fluid around the absorbent core between the outlet port and the inlet port. In some embodiments, the hydrophobic layer, the hydrophilic layer, or both may form a shell or envelope around the absorbent core. For example, the hydrophilic layer may be a first side of a non-woven textile, and the hydrophobic layer may be a second side of the non-woven textile, and the non-woven textile may be configured as an envelope around the absorbent core so the hydrophobic side is disposed against the absorbent core and the hydrophilic side is external to the envelope. The apparatus may additionally include a dressing in some embodiments, which can be fluidly coupled to the hydrophilic layer through an inlet port.

An apparatus for managing exudate is also described herein, wherein some example embodiments include an absorbent core, a hydrophobic shell disposed around the absorbent core, and a hydrophilic shell disposed around the hydrophobic shell. For example, the hydrophobic shell may be a first side of a non-woven textile, and the hydrophilic shell may be a second side of the non-woven textile. The non-woven textile may comprise or consist essentially of bonded polyester fibers, including hydrophilic polyester fibers. The hydrophobic shell, the hydrophilic shell, or both may form an envelope around the absorbent core in some example embodiments. The hydrophilic shell, the hydrophobic shell, or both, may also be adapted to manifold fluid around the absorbent core in some embodiments.

In yet other example embodiments, a wicking material such as a melamine formaldehyde foam or wicking fiber blocks can be used to distribute fluid in a canister, which can reduce or prevent fluid collection around a filter in certain orientations.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a tissue site in a position to receive treatment. However, as should be recognized by those skilled in the art, this frame of reference is merely a descriptive expedient rather than a strict prescription.

Figure 1:
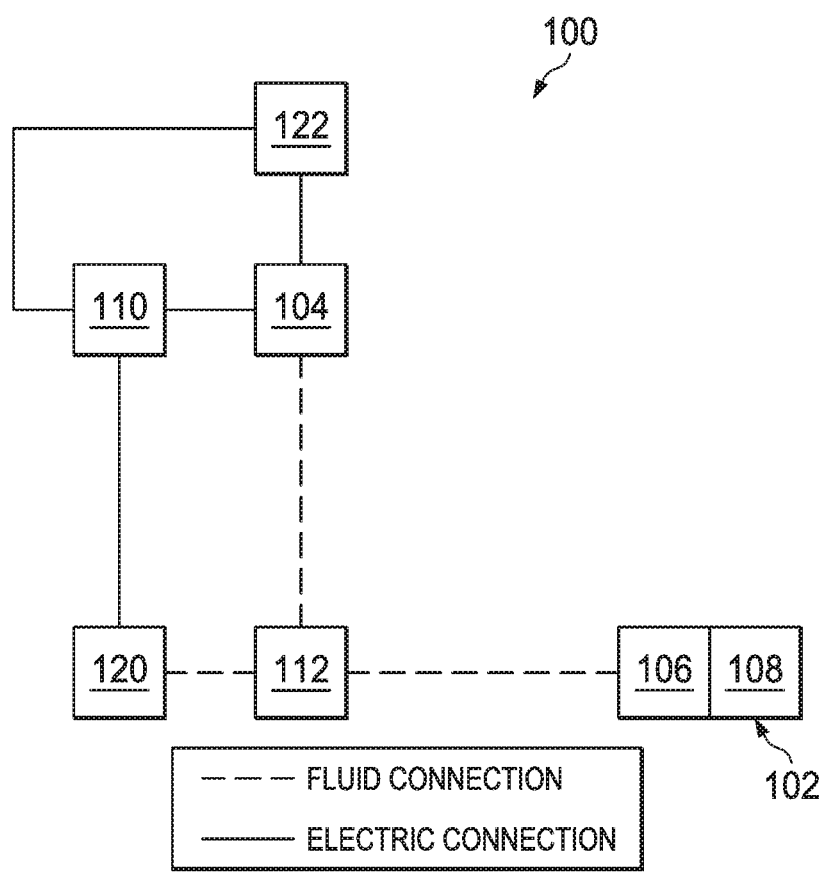
FIG. 1 is a functional block diagram of an example embodiment of a therapy system that can provide negative-pressure therapy in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, sub-acute, and dehisced wounds, incisions, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include negative-pressure supply, and may include or be configured to be coupled to a distribution component, such as a dressing or a container. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1. A dressing may include a cover, a tissue interface, or both in some embodiments. The dressing 102, for example, may include a cover 106 and a tissue interface 108. A regulator or a controller, such as a controller 110, may also be coupled to the negative-pressure source 104.

In some embodiments, a dressing interface may facilitate coupling the negative-pressure source 104 to the dressing 102. For example, such a dressing interface may be a T.R.A.C.® Pad or Sensa T.R.A.C.® Pad available from KCI of San Antonio, Tex. The therapy system 100 may also include a fluid container, such as a container 112, coupled to the dressing 102 and to the negative-pressure source 104.

Additionally, the therapy system 100 may include sensors to measure operating parameters and provide feedback signals to the controller 110 indicative of the operating parameters. As illustrated in FIG. 1, for example, the therapy system 100 may include a pressure sensor 120, an electric sensor 122, or both, coupled to the controller 110. The pressure sensor 120 may also be coupled or configured to be coupled to a distribution component and to the negative-pressure source 104.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may comprise or consist essentially of a substance or structure providing a plurality of pathways adapted to collect or distribute fluid under pressure. For example, the tissue interface 108 may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways may be interconnected to improve distribution or collection of fluids across a tissue site. In some illustrative embodiments, the tissue interface 108 may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, the tissue interface 108 may additionally or alternatively comprise projections that form interconnected fluid pathways. For example, the tissue interface 108 may be molded to provide surface projections that define interconnected fluid pathways.

The average pore size of a foam may vary according to needs of a prescribed therapy. For example, in some embodiments, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 120 or the electric sensor 122, are generally known in the art as any apparatus operable to detect or measure a physical phenomenon or property, and generally provide a signal indicative of the phenomenon or property that is detected or measured. For example, the pressure sensor 120 and the electric sensor 122 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 122 may optionally measure operating parameters of the negative-pressure source 104, such as the voltage or current, in some embodiments. Preferably, the signals from the pressure sensor 120 and the electric sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

Figure 2:
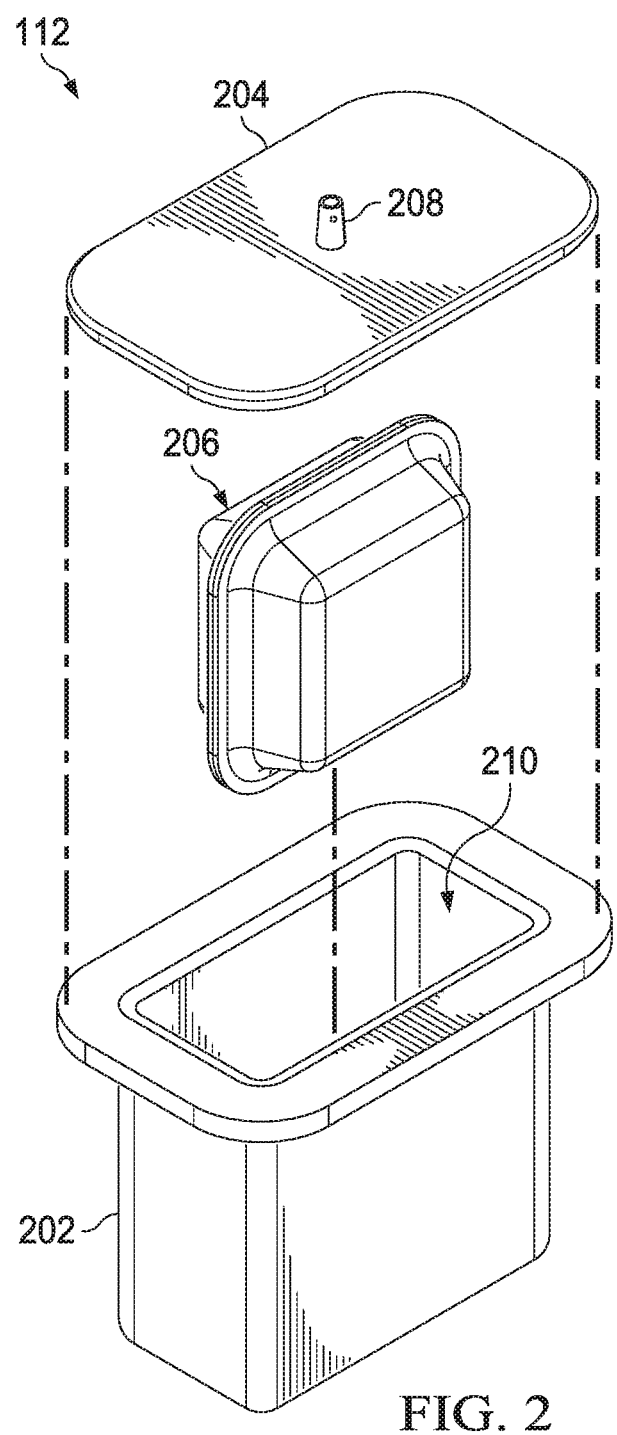
FIG. 2 is an assembly view of an example embodiment of a container of FIG. 1.

FIG. 2 is an assembly view of an example embodiment of the container 112. In the example embodiment of FIG. 2, the container 112 generally includes a casing, which may be formed by a canister 202 and a lid 204. A fluid management module may be disposed within the casing in some embodiments. The fluid management module may comprise or consist essentially of a bag, packet, pouch or other conformable package assembly. For example, as illustrated in the example embodiment of FIG. 2, the fluid management module may be a pouch 206, which can be disposed in a cavity 210 defined by the canister 202. The canister 202 and the lid 204 are preferably formed from material that is impermeable to fluid and sufficiently rigid to prevent collapse under negative pressure. For example, suitable materials may include plastics, thermoplastics, thermosets, ceramic, or metal. The lid 204 preferably includes an inlet port 208 configured to be fluidly coupled to a tissue site or distribution component, such as the dressing 102, for example, and to provide a fluid path through the lid 204.

Figure 3:
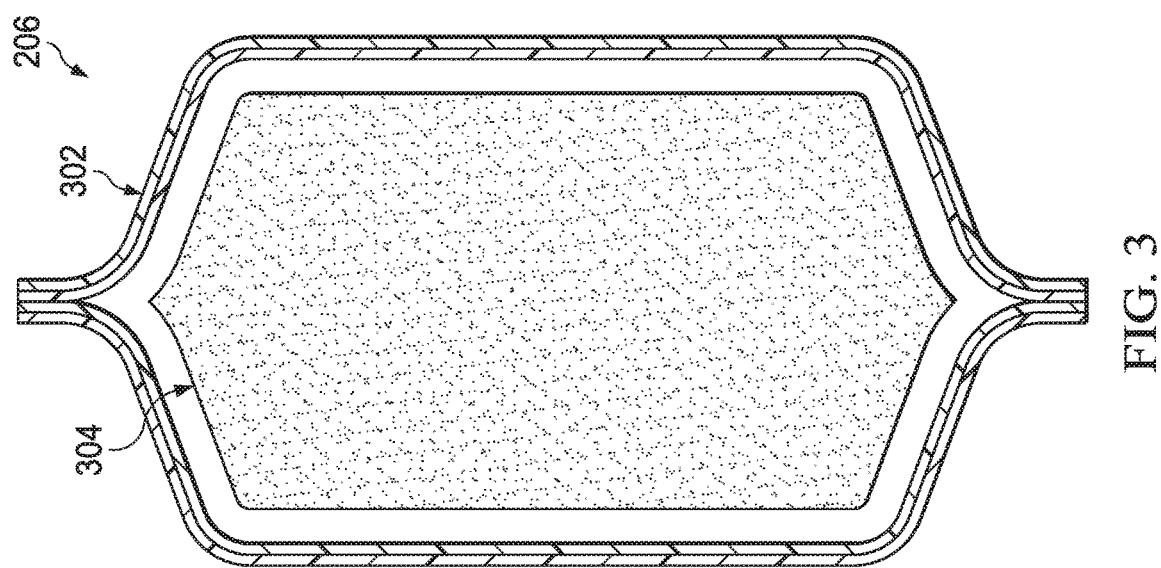
FIG. 3 is a schematic view of a cross-section of an example embodiment of a fluid management module of FIG. 2.

FIG. 3 is a schematic view of a cross-section of an example embodiment of the pouch 206, illustrating additional details that may be associated with some embodiments. The pouch 206 may, for example, comprise an absorbent core and a shell. The shell can substantially enclose the absorbent core, forming an envelope around the absorbent core in some embodiments to provide support or structural integrity to the absorbent core. The shell may also be a manifold in some embodiments, comprising or consisting essentially of a substance or structure providing a plurality of fluid pathways. In some illustrative embodiments, the pathways may be interconnected to improve distribution or collection of fluids across the shell.

In the example embodiment of FIG. 3, an absorbent core 304 is disposed within a shell represented as a distribution envelope 302. The distribution envelope 302 may be configured to manifold negative-pressure around the absorbent core 304. For example, the distribution envelope 302 may be a textile forming a porous envelope around the absorbent core 304 in some embodiments. In some illustrative embodiments, the distribution envelope 302 may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels that may be suitable for some example embodiments. The pouch 206 may be symmetrical in some embodiments, as illustrated in FIG. 3, but it need not be symmetrical. For example, the shape of the absorbent core 304 may be selected to conform to the shape of other embodiments of the container 112. The distribution envelope 302 may be adapted to allow the absorbent core 302 to expand if liquid is absorbed. For example, the distribution envelope 302 may be adapted to stretch or expand. Additionally or alternatively, the distribution envelope 302 may be larger than the absorbent core 304 if dry. In some embodiments, for example, the distribution envelope 302 may provide a margin of at least 5 millimeters around the absorbent core 304 for expansion. In some embodiments, the shape of the pouch 206 may be selected so that the distribution envelope 302 pushes against interior surfaces of the container 112 if the absorbent core 304 expands to capacity.

In some embodiments, the absorbent core 304 is preferably formed from a class of polymers known in the art as super-absorbent polymers, which can absorb and retain large amounts of liquid relative to their own mass, and may include hydrogels or hydrocolloids, for example. In certain exemplary embodiments, the absorbent core 304 preferably has basis weight between 400 grams per square meter and 800 grams per square meter, as measured by the EDANA 40.3-90 method. The absorbent core 304 may also have a free swell capacity in the range of 20 milliliters per gram and 50 milliliters per gram in some embodiments, as measured by the EDANA 440.2.02 method. In yet more specific example embodiments, the absorbent core 304 may have a free swell capacity of at least 40 milliliters per gram, as measured by the EDANA 440.2.02 method. Suitable materials may include sodium polyacrylates, cellulosics (carboxy methyl cellulose and salts, such as sodium CMC), or alginates. Suitable products may include the TEXSUS FP2696 absorbent, BASF 402C, or TECHNICAL ABSORBENTS 2317. However, the absorbent core 304 may be formed from any absorbent material suitable for holding, stabilizing, or solidifying wound exudate or other liquid, and may be selected based on cost or desired capacity, for example.

In some exemplary embodiments, the absorbent core 304 may be formed of granular absorbent components that may be scatter-coated onto a paper substrate. Scatter-coating involves spreading a granular absorbent powder uniformly onto a textile substrate, such as paper. The substrate, having the granular absorbent powder disposed thereon, may be passed through an oven to cure the powder and cause the powder to adhere to the paper substrate. The cured granular absorbent powder and substrate may be passed through a calender machine to provide a smooth uniform surface to the absorbent material.

Figure 4:
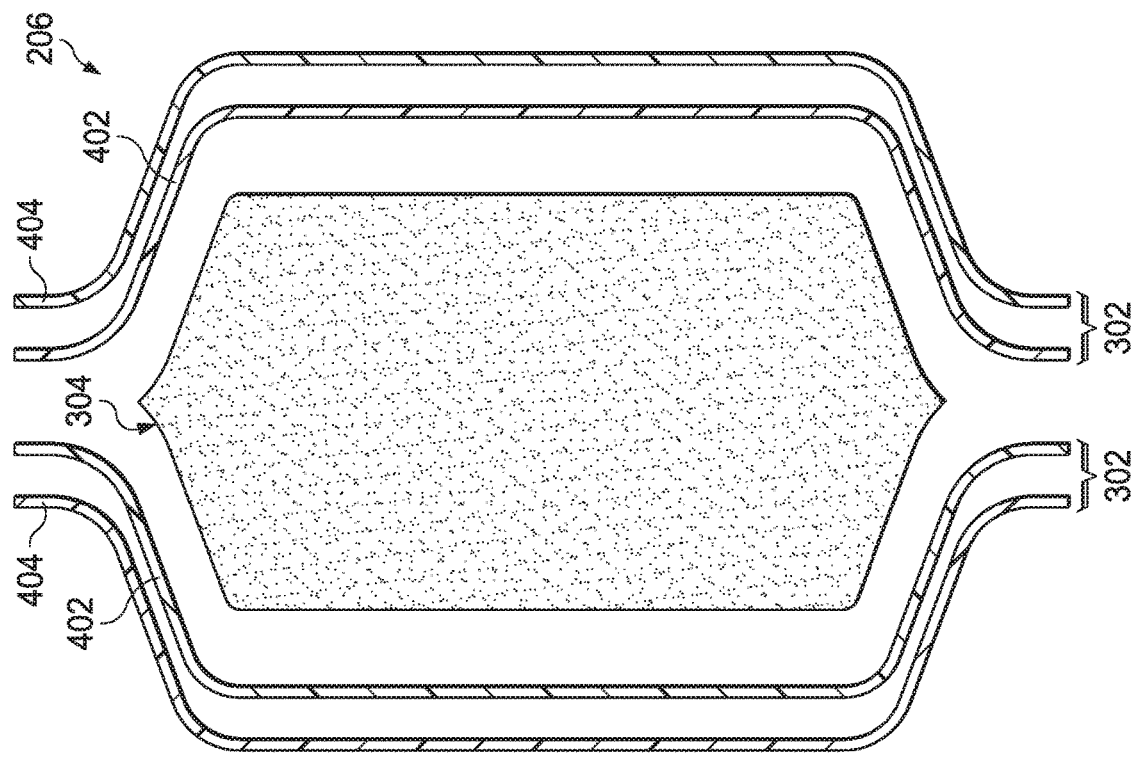
FIG. 4 is an exploded view of a cross-section of the fluid management module of FIG. 3.

FIG. 4 is an exploded view of the cross-section of the pouch 206 of FIG. 3, illustrating additional details that may be associated with some embodiments. As illustrated in FIG. 4, the distribution envelope 302 may comprise a hydrophobic layer 402 and a hydrophilic layer 404. In this context, a "hydrophilic layer" generally includes any layer comprising or consisting essentially of a material having an affinity for liquid, including exudate. Conversely, a "hydrophobic layer" generally includes any layer comprising or consisting essentially of a material having a tendency to repel liquid, including exudate. Hydrophobicity can also be defined by the geometry of water on a flat, static surface of a material. More specifically, hydrophobicity can be defined in terms of the angle between the edge of a droplet of liquid and the surface beneath the droplet, which may be referred to as the "contact angle." If the contact angle is greater than ninety degrees, so that the droplet forms a bead on the surface, the material may be classified as hydrophobic. However, if a droplet spreads on a surface, the contact angle is less than ninety degrees and the material is generally classified as hydrophilic.

Examples of suitable hydrophobic materials include hydrophobic polymers, such as polyester. Examples of suitable hydrophilic materials include hydrophilic polymers and hydrophobic polymers that have been physically or chemically modified to increase hydrophilicity, such as hydrophilic polyester. In some particular embodiments, for example, the hydrophobic layer 402 may comprise or consist essentially of a polyester textile, and the hydrophilic layer 404 may comprise or consist of a hydrophilic polyester textile.

In general, a textile includes any cohesive network of natural or synthetic fibers. For example, fibers may be woven, knitted, knotted, pressed together, or otherwise bonded to form a textile. Sheets or webs of fibers that are bonded together by entangling fibers mechanically, thermally, or chemically are generally classified as a non-woven textile. More broadly, though, a non-woven textile may include any sheet or layer of fibers which are neither woven nor knitted, such as felt, for example. Woven and non-woven textiles are generally porous, making them suitable as a manifold in some embodiments, but the porosity can be affected or selected based on fiber size and spacing, for example.

In the example embodiment of the distribution envelope 302 in FIG. 4, a first hydrophobic layer 402 and a second hydrophobic layer 402 may be disposed adjacent to the absorbent core 304. The first hydrophobic layer 402 and the second hydrophobic layer 402 may be coupled to each other to form a hydrophobic envelope around the absorbent core 304. For example, the absorbent core 304 may be disposed between the first hydrophobic layer 402 and the second hydrophobic layer 402, and the perimeters of the first hydrophobic layer 402 and the second hydrophobic layer 402 around the absorbent core 304 may be coupled by high-frequency welding, ultrasonic welding, heat welding, or impulse welding. As further illustrated in the example of FIG. 4, the distribution envelope 302 may also comprise a first hydrophilic layer 404 and a second hydrophilic layer 404. The first hydrophilic layer 404 and the second hydrophilic layer 404 may be disposed against the first hydrophobic layer 402 and the second hydrophobic layer 402, respectively, such that the hydrophobic layers 402 are disposed between the hydrophilic layers 404 and the absorbent core 304. The hydrophilic layers 404 are preferably directly coupled to the hydrophobic layers 402, but additionally or alternatively, the hydrophilic layers 404 may be coupled to each other to form a hydrophilic envelope enclosing the hydrophobic layers 402 and the absorbent core 304.

In other example embodiments, the configuration of hydrophobic and hydrophilic layers in the distribution envelope 302 may be varied. For example, in some embodiments, the hydrophilic layers 404 may be disposed adjacent to the absorbent core 304, and the hydrophobic layers 402 may be disposed adjacent to the hydrophilic layers 404 so that the hydrophilic layers 404 are disposed between the absorbent core 304 and the hydrophobic layers 402. In yet other embodiments, the distribution envelope 302 may have an asymmetrical configuration of hydrophobic layers 402 and hydrophilic layers 404. For example, in some embodiments, the distribution envelope may comprise an inner envelope, wherein the first hydrophobic layer 402 and the first hydrophilic layer 404 are disposed adjacent to the absorbent core 304, and an outer shell, wherein the second hydrophobic layer 402 is coupled to the first hydrophilic layer 404 and the second hydrophilic layer 404 is coupled to the first hydrophobic layer 402.

In some embodiments, the distribution envelope 302 may be a composite distribution layer having a hydrophobicity that varies from a first side to a second side. For example, in some embodiments, the hydrophobicity may increase from a first side to a second side of the distribution envelope. The hydrophobic layer 402 may be a first side of a composite distribution layer, and the hydrophilic layer 404 may be a second side of the composite distribution layer in some embodiments, which can increase the hydrophobicity of the distribution envelope 302 from an external side to an internal side. For example, the distribution envelope 302 may be a non-woven textile, the hydrophobic layer 402 may be a first side of the non-woven textile, and the hydrophilic layer 404 may be a second side of the non-woven textile. More specifically, in some example embodiments, the distribution envelope 302 may comprise or consist essentially of a dual-layer non-woven textile, such as a through-air bonded web of dry polyester and hydrophilic, profiled polyester and bi-component fibers. Suitable products may include the DRYWEB TDL2 acquisition and distribution layer from LIBELTEX, or the SLIMCORE TL4 acquisition and distribution layer from LIBELTEX, for example.

The distribution envelope 302 is preferably sufficiently porous to distribute fluid while also maintaining integrity of the absorbent core 304. For example, in some embodiments, pores or channels of about 50 microns to 400 microns may be suitable for the distribution envelope 302, and 100 microns may be particularly advantageous for some applications. Additionally or alternatively, pore sizes may vary across the distribution envelope 302. In some embodiments, a first layer or side of the distribution envelope 302 may have pores that are smaller than pores in a second layer or side. For example, the distribution envelope 302 may have an inner envelope with pores of about 50 microns suitable for retaining super-absorbent particles of the absorbent core, and an outer shell with pores of about 400 microns for distributing fluid.

Figure 5:
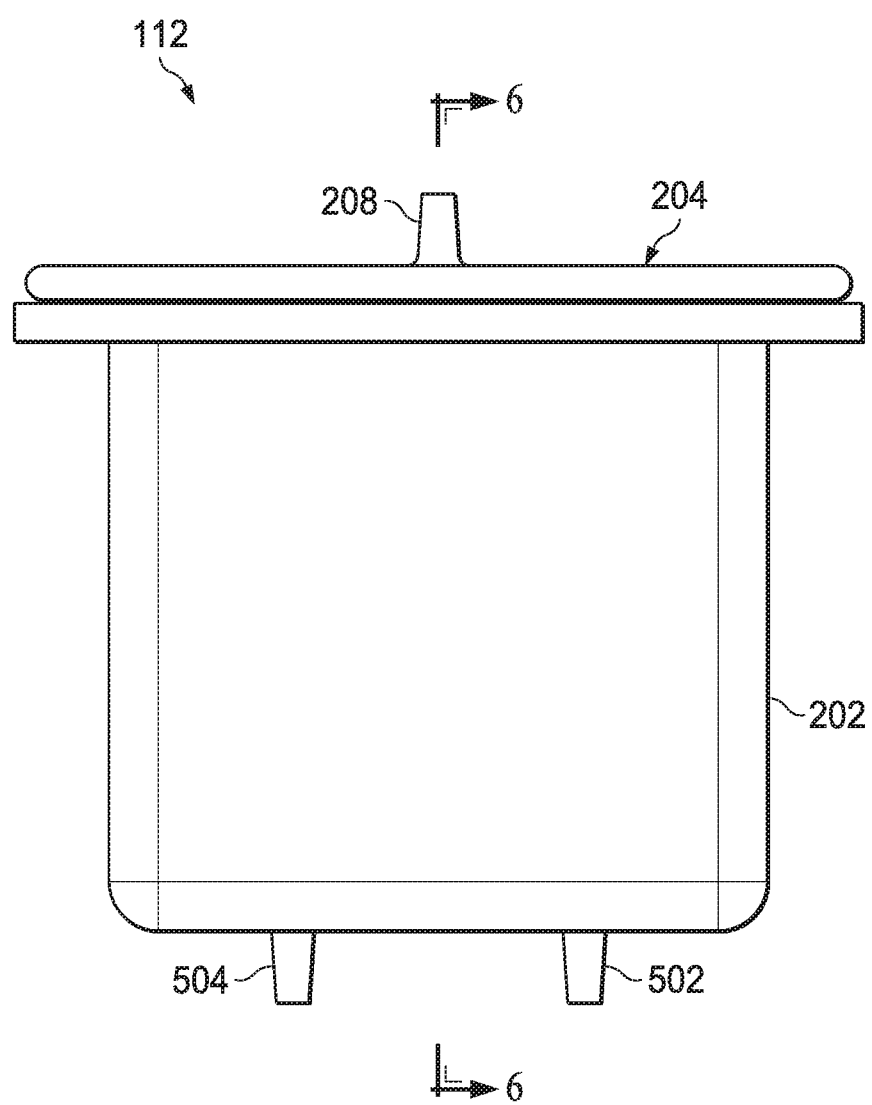
FIG. 5 is an assembled front view of the example embodiment of the container of FIG. 2.

FIG. 5 is an assembled front view of the example embodiment of the container 112 of FIG. 2, illustrating additional details that may be associated with some embodiments. As illustrated in FIG. 5, the container 112 may comprise one or more outlet ports, such as an outlet port 502 and an outlet port 504, which may be configured to be coupled to upstream components and to provide a fluid path through the canister 202. The lid 204 may be coupled to the canister 202, and is preferably sealed to the canister 202 to fluidly isolate the cavity 210 from the external environment so that fluid may only enter and exit the container 112 through the inlet port 208, the outlet port 502, and the outlet port 504. In some embodiments, the lid 204 may be welded, glued, or otherwise permanently fastened to the canister 202 to deter or prevent tampering with the pouch 206. In other embodiment, the lid 204 may be releasably fastened to the canister 202 to facilitate inserting and removing the pouch 206. For example, the lid 204 and the canister 202 may be threaded or sized for an interference fit, with suitable O-rings providing a fluid seal.

Figure 6:
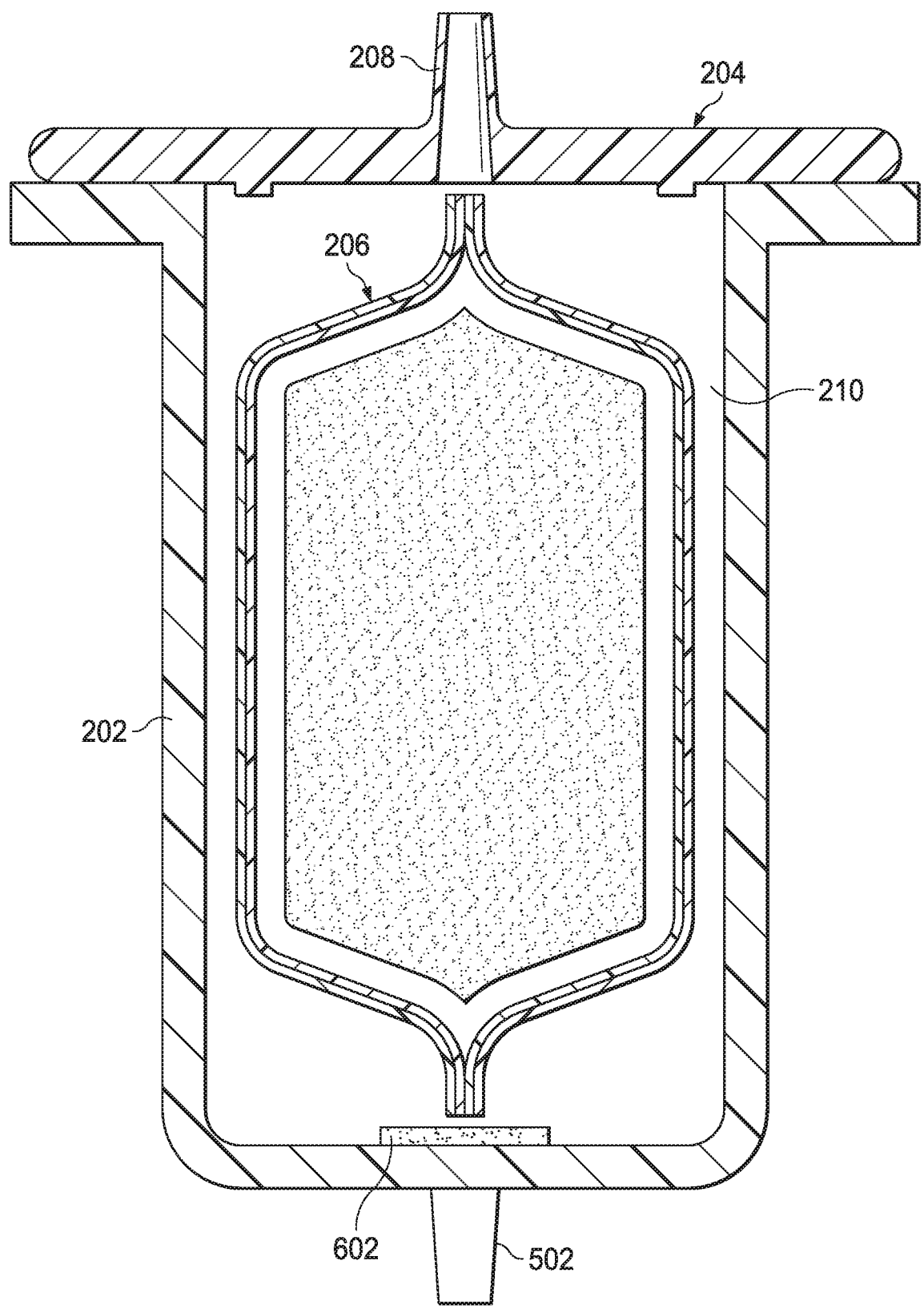
FIG. 6 is a cross-section of the example container in FIG. 5.

FIG. 6 is a cross-section of the container 112 in FIG. 5 taken along line 6-6, illustrating additional details that may be associated with some embodiments of the container 112. For example, as shown in FIG. 6, the lid 204 may be coupled to the canister 202 to close the cavity 210 and form a collection chamber defined by interior surfaces of the canister 202 and the lid 204. The pouch 206 may be disposed in the collection chamber in fluid communication with the inlet port 208 and the outlet port 502.

The container 112 may also include a filter 602 configured to block liquid from exiting the container 112 through the outlet port 502. In one illustrative embodiment, the filter 602 may be a hydrophobic membrane or material that allows the transmission of gases but substantially prevents the transmission of liquids through the filter 602. Additionally or alternatively, the filter 602 may comprise or consist essentially of a permeable material that is coated with a hydrophobic substance to make the material substantially impermeable to liquid. In some embodiments, the filter 602 may be a chemically bonded fluorocarbon monomer using a plasma process, thus increasing the hydrophobicity. The filter 602 may also be oleophobic or lipophobic, or coated with an oleophobic or lipophobic substance. The oleophobicity or lipophobicity contributes to the ability of the filter 602 to wick or shed exudate and other fluid if the filter 602 is incidentally contacted by the liquid. Some exemplary materials that may be used to separate liquid and gas include, without limitation, expanded polytetrafluoroethylene (ePTFE), polytetrafluoroethylene (PTFE), foam, spun fiberglass, cotton gauze, polyester, glass fibers, polypropylene, microfibers, porous polymeric membranes, or any other materials or substances that are hydrophobic, oleophobic, or lipophobic in nature.

In some embodiments, the inlet port 208 may be fluidly coupled to the dressing 102, and the outlet port 502 may be fluidly coupled to the negative-pressure source 104 or another upstream component. The outlet port 504 may be fluidly coupled to the pressure sensor 120 in some embodiments.

In operation, negative pressure from the negative-pressure source 104 can be distributed to the dressing 102 through the container 112, drawing exudate and other fluid through the inlet port 208 into the cavity 210. The hydrophobic layer 402 may be configured to distribute fluid drawn through the inlet port 208 across the distribution envelope 302. The hydrophobic layer 402 may also be characterized as a wicking side, wicking surface, distribution surface, distribution side, or fluid distribution surface. The hydrophobic layer 402 may be a smooth surface configured to move fluid through the distribution envelope 302 along a grain of the distribution envelope 302. The hydrophilic layer 404 may be configured to acquire fluid from the hydrophobic layer 402 to facilitate fluid movement into the absorbent core 304. The hydrophilic layer 404 may also be characterized as a fluid acquisition surface, fluid acquisition side, hydrophilic acquisition surface, or hydrophilic acquisition side. The hydrophilic layer 404 may be a fibrous surface and be configured to draw fluid into the distribution envelope 302.

Fluid can enter the container 112 through the inlet port 208. Gas may egress the container 112 through the outlet port 502, the outlet port 504, or both in some embodiments, and the filter 602 can prevent or substantially limit flow of liquid through the outlet port 502 and the outlet port 504. Liquid can be effectively captured by the distribution envelope 302 as it moves through the container 112, or if the volume of liquid in the container 112 increases, and the distribution envelope 302 can distribute liquid to the absorbent core 304 for storage. The absorbent core 304 may swell if liquid is absorbed, and may push the distribution envelope 302 against the container 112 as it expands. The distribution envelope 302 can provide a fluid path around the absorbent core 304 between the inlet port 208 and the outlet port 502, even if the absorbent core 304 expands and presses the distribution envelope 302 against interior surfaces of the container 112.

Figure 7:
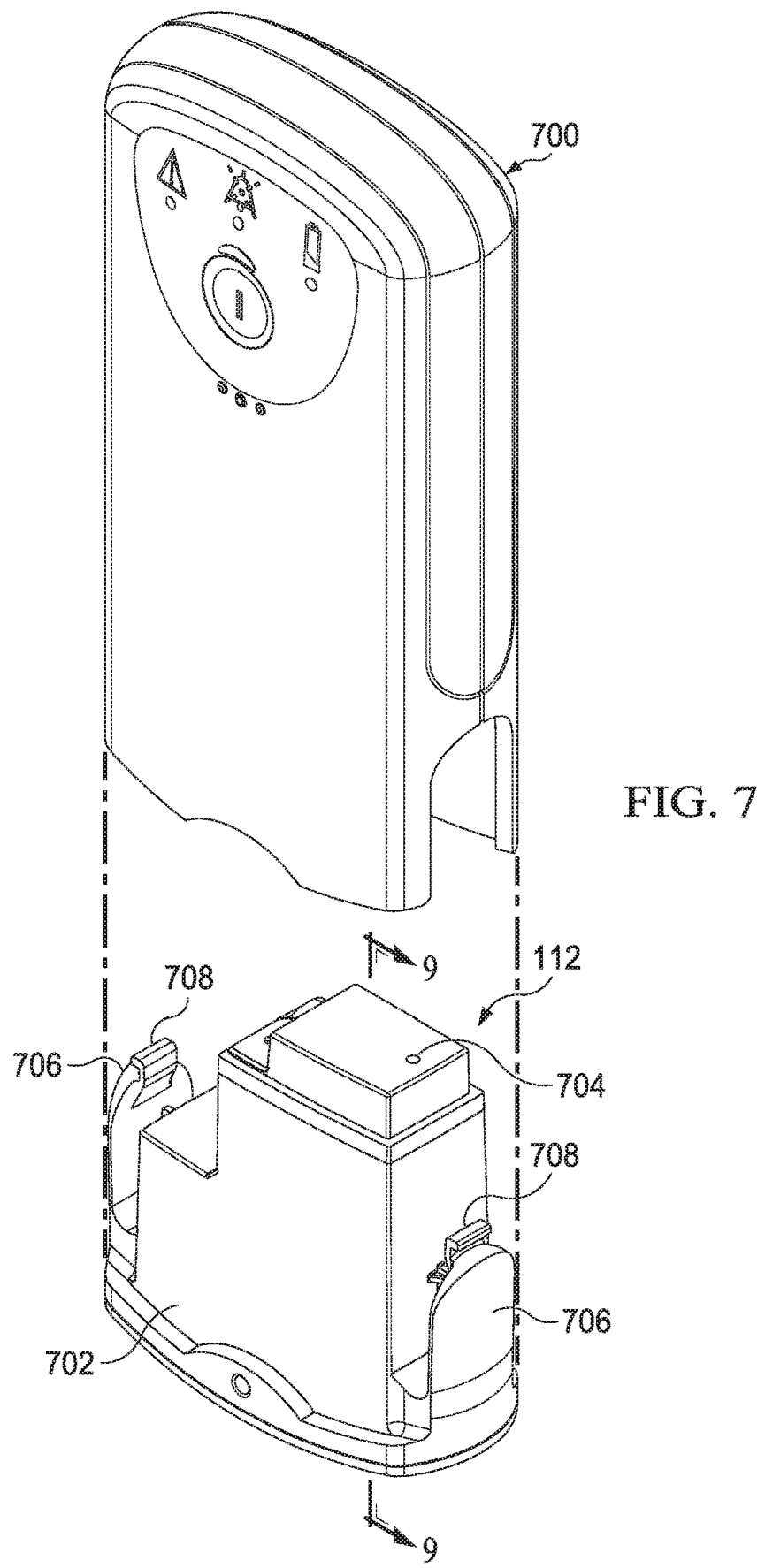
FIG. 7 is an assembly view of an example embodiment of a therapy unit and another example embodiment of the container of FIG. 1.

FIG. 7 is an assembly view of an example embodiment of a therapy unit 700 and another example embodiment of the container 112, illustrating additional details that may be associated with some embodiments of the therapy system 100. In the example embodiment of FIG. 7, the container 112 generally comprises a casing 702 and an outlet port 704. The outlet port 704 may be configured for fluid coupling with a negative-pressure source (not visible in FIG. 7) associated with the therapy unit 700. For example, the therapy unit 700 may comprise an integral negative-pressure source and an internal port configured to couple the negative-pressure source to the outlet port 704 if the container 112 is inserted into the therapy unit 700. In some embodiments, the container 112 may additionally include one or more attachment tabs 706 and locking clips 708. The attachment tabs 706 and respective locking clips 708 may be configured to engage compatible detents or hardware within the therapy unit 700 if the container 112 is inserted into the therapy unit 700.

Figure 8:
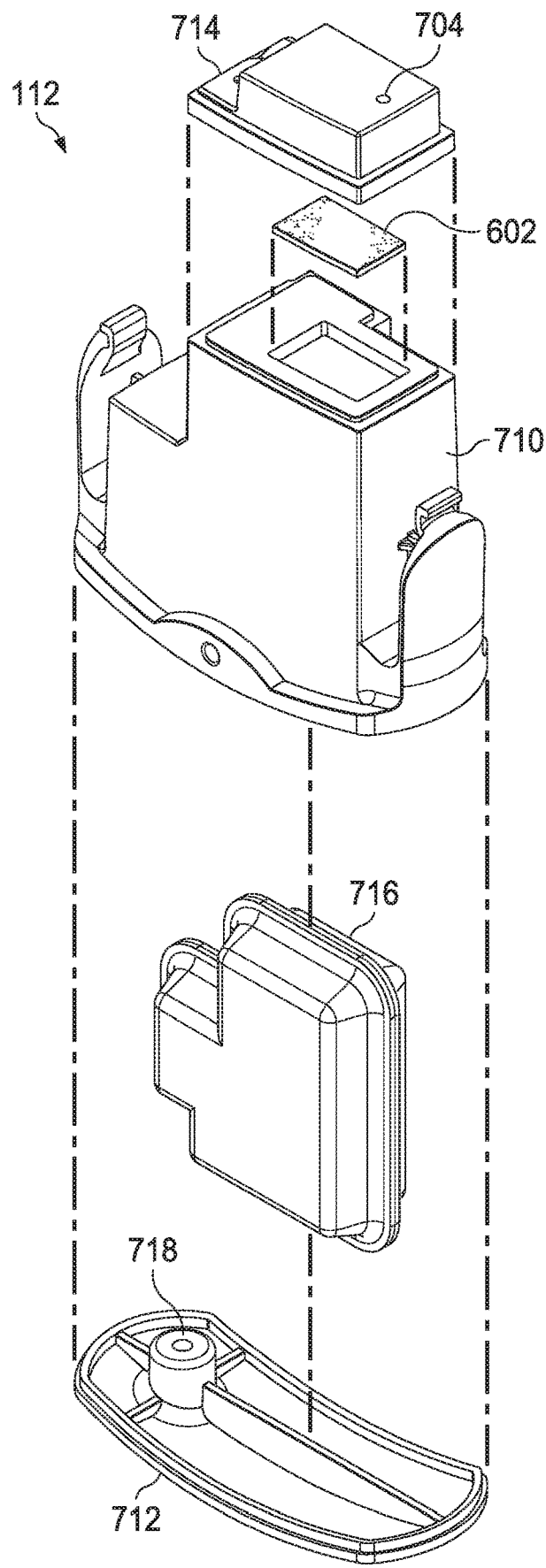
FIG. 8 is an assembly view of the example embodiment of the container of FIG. 7.

FIG. 8 is an assembly view of the example embodiment of the container 112 of FIG. 7, illustrating additional details that may be associated with some embodiments. As illustrated in FIG. 8, the casing 702 may comprise a canister 710, a base 712, and a cap 714. The container 112 also preferably comprises a filter 602 disposed over the outlet port 704. A fluid management module may be disposed within the canister 710 in some embodiments. For example, as illustrated in the example embodiment of FIG. 8, the fluid management module may be a packet 716, which may be similar or analogous to the pouch 206 in some embodiments. In some embodiments, the base 712, the cap 714, or both may be integrally molded with the canister 710, but in other embodiments either the base 712, the cap 714, or both may be removably coupled to the canister 710 to facilitate inserting or removing the packet 716.

As shown in FIG. 8, the container 112 may also comprise an inlet port 718. The outlet port 704 can be disposed in the cap 714 and the inlet port 718 may be disposed in the base 712, as illustrated in the example of FIG. 8. However, the configuration and position of the outlet port 704 and the inlet port 718 may vary in other embodiments.

Figure 9:
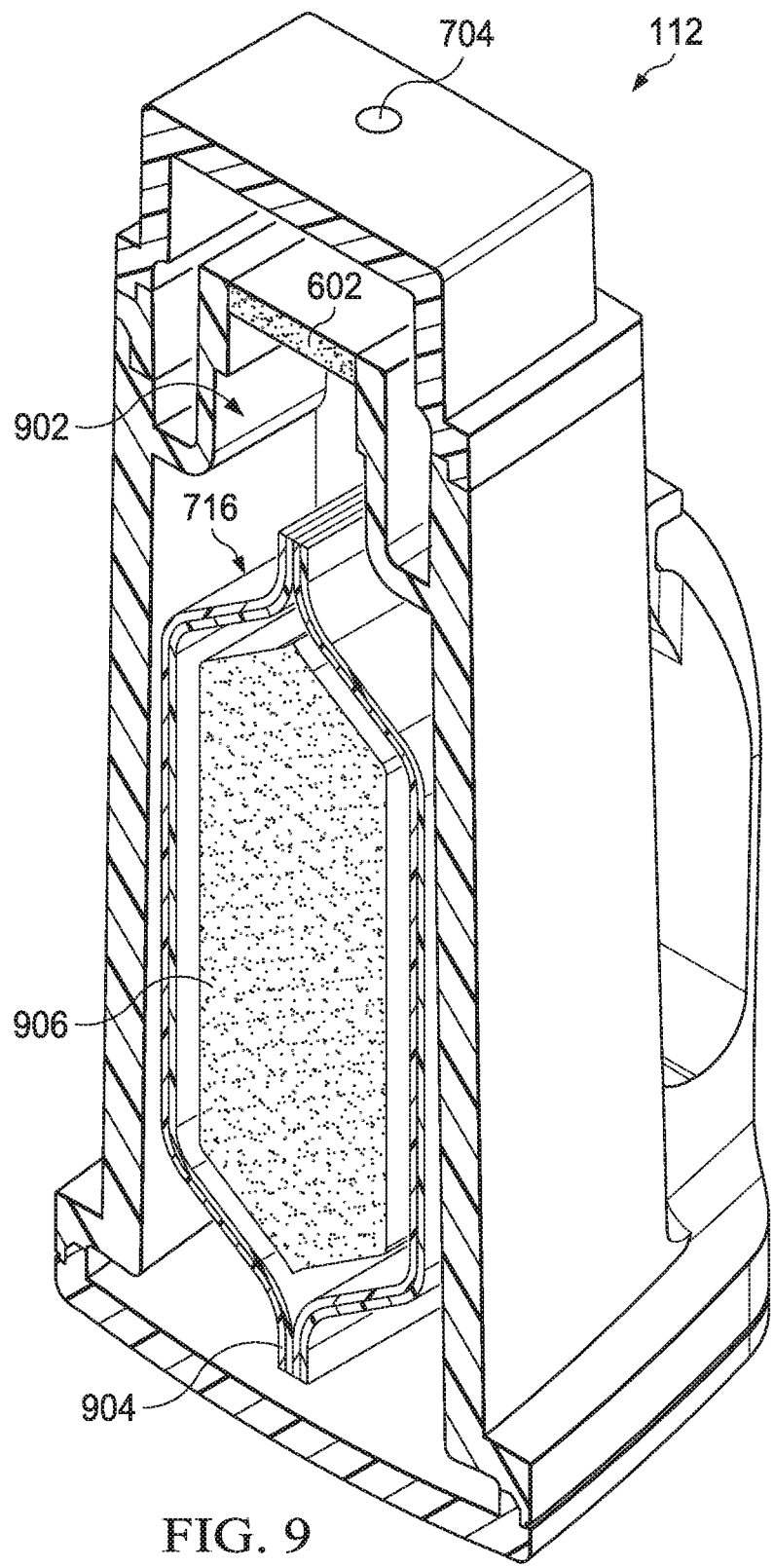
FIG. 9 is a cross-section view of the example container in FIG. 7.

FIG. 9 is a cross-section view of the container 112 in FIG. 7 taken along line 9-9, illustrating additional details that may be associated with some embodiments of the container 112. For example, interior surfaces of the container 112 may form a collection chamber 902, and the packet 716 may be disposed in the collection chamber 902 in fluid communication with the outlet port 704 and the inlet port 718 (not shown).

Additional details of an example embodiment of the packet 716 are also illustrated in FIG. 9. For example, the packet 716 may include a distribution envelope 904 and an absorbent core 906. The distribution envelope 904 and the absorbent core 906 may be similar or analogous to the distribution envelope 302 and the absorbent core 304 in many respects. For example, the distribution envelope 904 may comprise a hydrophilic side and a hydrophobic side to acquire and distribute liquid to the absorbent core 906, substantially as described above with respect to the pouch 206.

In some embodiments, the dressing 102 may be fluidly coupled to the inlet port 718, and the negative-pressure source 104 may be fluidly coupled to the outlet port 704. The pressure sensor 120 may also be fluidly coupled to the container 112, in some embodiments, such as through a secondary port in the casing 702.

In operation, negative pressure from the negative-pressure source 104 can be distributed to the dressing 102 through the container 112, drawing exudate and other fluid through the inlet port 718 into the collection chamber 902. The distribution envelope 904 may be configured to distribute fluid drawn through the inlet port 718 across the packet 716, and to facilitate fluid movement into the absorbent core 906.

Fluid can enter the container 112 through the inlet port 718. Gas may egress the container 112 through the outlet port 704, and the filter 602 can prevent or substantially limit flow of liquid through the outlet port 704. Liquid can be effectively captured by the distribution envelope 904 as it moves through the container 112, or if the volume of liquid in the container 112 increases, and the distribution envelope 904 can distribute liquid to the absorbent core 906 for storage. The absorbent core 906 may swell if liquid is absorbed, and may push the distribution envelope 904 against the casing 702 as it expands. The distribution envelope 904 can provide a fluid path around the absorbent core 906 between the inlet port 718 and the outlet port 704, even if the absorbent core 906 expands and presses the distribution envelope 904 against interior surfaces of the container 112.

The systems, apparatuses, and methods described herein may provide significant advantages. For example, conventional exudate containers often fail if the orientation is changed, which can be common for mobile patients, or may use multiple filters to maintain operation in multiple orientations, which can significantly increase manufacturing cost and decrease fluid capacity. A container such as the container 112 can overcome these shortcomings and others. For example, the container 112 can be used in multiple orientations, but the cost of manufacturing can be significantly reduced by reducing the number of filters.

While shown in a few illustrative embodiments, a person having ordinary skill in the art will recognize that the systems, apparatuses, and methods described herein are susceptible to various changes and modifications. Features, elements, and aspects described or illustrated in the context of some example embodiments may be omitted, or combined with features, elements, and aspects of other example embodiments unless indicated otherwise. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An exudate container, comprising:
    a rigid casing that is fluid impermeable;
    an absorbent core disposed within the casing, wherein the absorbent core is configured to absorb and retain liquid;
    a manifold disposed in the casing and enclosing the absorbent core, the manifold comprising a hydrophobic envelope enclosing the absorbent core and a hydrophilic envelope enclosing the hydrophobic envelope, the hydrophobic envelope coupled to the hydrophilic envelope, wherein:
        the manifold is larger than the absorbent core and provides a margin between the absorbent core and the manifold;
        the absorbent core is configured to swell in response to absorbing liquid; and
        the manifold is configured to provide a fluid path around the absorbent core in the event the absorbent core expands and presses the manifold against the rigid casing;
    an inlet port fluidly coupled to the manifold; and
    an outlet port fluidly coupled to the manifold.

2. The exudate container of claim 1, wherein the manifold comprises a non-woven textile.

3. The exudate container of claim 1, wherein the manifold comprises a textile of polyester fibers.

4. The exudate container of claim 1, wherein the manifold consists essentially of polyester fibers.

5. The exudate container of claim 1, wherein the manifold consists essentially of polyester fibers forming a porous envelope around the absorbent core.

6. The exudate container of claim 1, wherein the manifold comprises bonded polyester fibers.

7. The exudate container of claim 1, wherein the absorbent core comprises a super-absorbent polymer.

8. The exudate container of claim 1, wherein the manifold comprises a dual-layer non-woven textile of dry polyester and hydrophilic, profiled polyester and bi-component fibers.

9. The exudate container of claim 1, further comprising:
    a single filter configured to block liquid transmission through the outlet port.

10. The exudate container of claim 1, wherein:
    the manifold comprises a distribution manifold;
    the hydrophobic envelope is an inner envelope having pores of about 50 microns; and the hydrophilic envelope is an outer shell having pores of about 400 microns.

11. An apparatus for providing negative-pressure therapy, the apparatus comprising:
    a negative-pressure source;
    a rigid fluid-impermeable container comprising an outlet port fluidly coupled to the negative-pressure source;
    a hydrophilic layer disposed in the container and fluidly coupled to the outlet port;
    an absorbent core disposed in the container, wherein the absorbent core is configured to absorb and retain liquid;
    a hydrophobic layer disposed between the absorbent core and the hydrophilic layer, wherein the hydrophobic layer forms a first envelope around the absorbent core and the hydrophobic layer forms a second envelope around the hydrophobic layer; and
    a gap between a planar side of the hydrophobic layer and a planar side of the absorbent core.

12. The apparatus of claim 11, wherein the container further comprises an inlet port fluidly coupled to the hydrophilic layer, and the hydrophilic layer is configured to manifold fluid around the absorbent core between the outlet port and the inlet port.

13. The apparatus of claim 11, wherein the hydrophilic layer is coupled to the hydrophobic layer.

14. The apparatus of claim 11, wherein:
    the hydrophilic layer comprises bonded hydrophilic polyester fibers;
    the hydrophobic layer comprises bonded polyester fibers; and
    the absorbent core comprises a super-absorbent polymer.

15. The apparatus of claim 11, wherein:
    the hydrophilic layer comprises woven hydrophilic polyester fibers;
    the hydrophobic layer comprises woven polyester fibers; and
    the absorbent core comprises a super-absorbent polymer.

16. The apparatus of claim 11, wherein:
    the hydrophilic layer is a first side of a non-woven textile; and
    the hydrophobic layer is a second side of the non-woven textile.

17. The apparatus of claim 11, further comprising:
    an inlet port fluidly coupled to the hydrophilic layer; and
    a dressing configured to be coupled to the inlet port.

18. The apparatus of claim 11, wherein:
the hydrophobic layer has pores of about 50 microns; and
the hydrophilic layer has pores of about 400 microns.

19. A method for managing fluid in a rigid fluid-impermeable canister of a negative-pressure therapy system, the method comprising:
- receiving fluid through an inlet port of the canister;
- capturing liquid from the fluid in a distribution envelope fluidly coupled to the inlet port, wherein the distribution envelope comprises a distribution layer and an acquisition layer coupled to the distribution layer, wherein the distribution layer is a hydrophobic shell and the acquisition layer is a hydrophilic shell;
- transferring the liquid from the distribution envelope to an absorbent core enclosed within the distribution envelope, wherein the distribution layer encloses the absorbent core, the acquisition layer encloses the distribution layer, and a space is provided between the distribution envelope and the absorbent core;
- swelling the absorbent core within the space between the distribution envelope and the absorbent core in response to liquid being absorbed by and retained in the absorbent core; and
- transmitting gas from the fluid through an outlet port of the canister.

20. The method of claim 19, further comprising filtering the fluid to prevent liquid from egressing through the outlet port.

21. The method of claim 19, further comprising pushing the distribution envelope against the canister by the absorbent core in response to swelling of the absorbent core.

* * * * *

UNITED STATES PATENT AND TRADEMARK OFFICE
CERTIFICATE OF CORRECTION

PATENT NO. : 11,413,389 B2
APPLICATION NO. : 15/741578
DATED : August 16, 2022
INVENTOR(S) : Christopher Brian Locke Page 1 of 1

It is certified that error appears in the above-identified patent and that said Letters Patent is hereby corrected as shown below:

In the Claims

Column 16
Line 37, In Claim 11, delete "hydrophobic layer" and insert -- hydrophilic layer --, therefor.

Signed and Sealed this
Ninth Day of April, 2024

Katherine Kelly Vidal
*Director of the United States Patent and Trademark Office*